United States Patent
Chavan et al.

(10) Patent No.: US 11,850,019 B2
(45) Date of Patent: Dec. 26, 2023

(54) ANALYTE MONITORING SYSTEM

(71) Applicant: Senseonics, Incorporated, Germantown, MD (US)

(72) Inventors: Abhi Chavan, Germantown, MD (US); Barkha Raisoni, Germantown, MD (US); Robert Matikyan, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 890 days.

(21) Appl. No.: 16/567,271

(22) Filed: Sep. 11, 2019

(65) Prior Publication Data

US 2020/0077891 A1 Mar. 12, 2020

Related U.S. Application Data

(60) Provisional application No. 62/729,754, filed on Sep. 11, 2018.

(51) Int. Cl.
*A61B 5/00* (2006.01)
*A61B 5/145* (2006.01)
*A61M 5/172* (2006.01)
*H04W 4/38* (2018.01)
(Continued)

(52) U.S. Cl.
CPC .......... *A61B 5/0004* (2013.01); *A61B 5/0031* (2013.01); *A61B 5/14532* (2013.01); *A61B 5/681* (2013.01); *A61B 5/742* (2013.01); *A61M 5/1723* (2013.01); *H04W 4/38* (2018.02);
(Continued)

(58) Field of Classification Search
CPC ... A61B 5/0004; A61B 5/14532; A61B 5/742; A61B 5/7435; A61M 5/1723; A61M 2205/3584; A61M 5/14244; A61M 2205/50; A61M 2205/502; H04W 4/38; H04W 76/15; H04W 76/19; H04W 4/80
See application file for complete search history.

(56) References Cited

U.S. PATENT DOCUMENTS

| | | |
|---|---|---|
| 8,073,548 B2 | 12/2011 | Colvin, Jr. et al. |
| 9,414,775 B2 | 8/2016 | Colvin, Jr. et al. |
| 9,693,714 B2 | 7/2017 | DeHennis et al. |

(Continued)

FOREIGN PATENT DOCUMENTS

EP 3310067 A1 4/2018

*Primary Examiner* — Tse W Chen
*Assistant Examiner* — Clarissa Cuevas
(74) *Attorney, Agent, or Firm* — Rothwell, Figg, Ernst & Manbeck, P.C.

(57) ABSTRACT

An analyte monitoring system may include an analyte sensor, two or more devices including a display device and a second device, and a transceiver. The transceiver may be configured to (i) receive measurement information from the analyte sensor, (ii) establish a connection with the display device while being connected with no other device of the two or more devices, (iii) convey first information to the display device while connected with the display device, (iv) establish a connection with the second device while being connected with no other device of the two or more devices, and (v) convey or receive second information to or from the second device while connected with the second device. The display device may be configured to (i) receive the first information from the transceiver and (ii) display an analyte level based on at least the first information.

34 Claims, 8 Drawing Sheets

(51) Int. Cl.
*H04W 76/15* (2018.01)
*H04W 76/19* (2018.01)

(52) U.S. Cl.
CPC ........... *H04W 76/15* (2018.02); *H04W 76/19* (2018.02); *A61M 2205/3584* (2013.01)

(56) References Cited

U.S. PATENT DOCUMENTS

| | | | |
|---|---|---|---|
| 10,022,499 B2 | 7/2018 | Galasso | |
| 10,052,049 B2 | 8/2018 | Blomquist et al. | |
| 10,064,030 B2* | 8/2018 | Park | H04W 4/80 |
| 10,987,178 B2* | 4/2021 | Shelton, IV | A61B 34/37 |
| 2013/0241745 A1 | 9/2013 | Colvin, Jr. et al. | |
| 2014/0112326 A1 | 4/2014 | Torikai et al. | |
| 2016/0345874 A1 | 12/2016 | Raisoni et al. | |
| 2019/0132801 A1* | 5/2019 | Kamath | A61B 5/686 |
| 2020/0359944 A1* | 11/2020 | Raisoni | A61B 5/742 |
| 2021/0153001 A1* | 5/2021 | Eisner | H04W 4/90 |

* cited by examiner

ANALYTE MONITORING SYSTEM

CROSS-REFERENCE TO RELATED APPLICATION

The present application claims the benefit of priority to U.S. Provisional Application Ser. No. 62/729,754, filed on Sep. 11, 2018, which is incorporated herein by reference in its entirety.

BACKGROUND

Field of Invention

Aspects of the present invention relate to systems and methods for analyte monitoring. Specifically, aspects of the present invention may relate to connections between multiple devices in an analyte monitoring system.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels<7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations comprising, but not limited to, integrating multiple devices into an analyte monitoring system.

SUMMARY

One aspect of the invention may provide an analyte monitoring system including an analyte sensor, two or more devices including a display device and a second device, and a transceiver. The transceiver may be configured to (i) receive measurement information from the analyte sensor, (ii) establish a connection with the display device while being connected with no other device of the two or more devices, (iii) convey first information to the display device while connected with the display device, (iv) establish a connection with the second device while being connected with no other device of the two or more devices, and (v) convey or receive second information to or from the second device while connected with the second device. The display device may be configured to (i) receive the first information from the transceiver and (ii) display an analyte level based on at least the first information, and the second device may be configured to receive or convey the second information from or to the transceiver.

In some embodiments, the display device may be further configured to terminate the connection with the transceiver if any of one or more disconnection events occur. In some embodiments, the display device may executes a mobile medical application (MMA), and the one or more disconnection events may include the MMA transitioning from being run in the foreground to running in the background. In some embodiments, the one or more disconnection events may include the display device detecting an available connection with the second device. In some embodiments, the transceiver may be further configured to establish the connection with the second device in response to the display device terminating the connection with the transceiver.

In some embodiments, the transceiver may comprise a memory, and the transceiver may be further configured to store an identification of each of the two or more devices in the memory and transition between connections with the identified two or more devices at scheduled intervals. In some embodiments, the transceiver may be further configured to transition from being connected to the display device to being connected to the second device and from being connected to the second device to being connected to the display device at scheduled intervals. In some embodiments, the transceiver may be further configured to transition from being connected to the second device to being connected to the display device by terminating the connection with the second device and establishing the connection with the display device. In some embodiments, the transceiver may be further configured to transition from being connected to the display device to being connected to the second device by terminating the connection with the display device and establishing the connection with the second device.

In some embodiments, the transceiver may be further configured to establish the connection with the display device by conveying one or more advertising packets and waiting for the display device to connect to the transceiver. In some embodiments, the transceiver further may be configured to establish the connection with the second device by conveying one or more advertising packets and waiting for the second device to connect to the transceiver. In some embodiments, the transceiver may be further configured to establish the connection with the second device by receiving one or more advertising packets from the second device and connecting to the second device. In some embodiments, the two or more devices may further include a third device, and the transceiver may be further configured to establish a connection with the third device while being connected with no other device of the two or more devices and convey or receive third information to or from the third device while connected with the third device.

In some embodiments, the second device may comprise an insulin pump, a blood glucose meter, or a wearable. In some embodiments, the transceiver may be further configured to calculate an analyte level using at least the received measurement information, the first information may include the calculated analyte level, and the analyte level displayed by the display device may be the calculated analyte level. In some embodiments, the first information may include the measurement information, and the display device may be further configured to calculate the displayed analyte level using at least the measurement information.

Another aspect of the invention may provide a transceiver including a sensor interface, a device interface, and a computer. The sensor interface may be configured to receive measurement information from an analyte sensor. The device interface may be configured to convey or receive information from two or more devices, and the two or more devices may include a display device and a second device. The computer may include a non-transitory memory and a processor. The computer may be configured to: (i) use the device interface to establish a connection with the display device while being connected with no other device of the two or more devices, (ii) use the device interface to convey first information to the display device while connected with the display device, (iii) use the device interface to establish a connection with the second device while being connected with no other device of the two or more devices, and (iv) use the device interface to convey or receive second information to or from the second device while connected with the second device.

In some embodiments, the computer may be further configured to use the device interface to establish the connection with the second device in response to the display device terminating the connection with the transceiver. In some embodiments, the computer may be further configured to store an identification of each of the two or more devices in the memory and use the device interface to transition between connections with the identified two or more devices at scheduled intervals.

In some embodiments, the computer may be further configured to use the device interface to transition from being connected to the display device to being connected to the second device and from being connected to the second device to being connected to use the display device at scheduled intervals. In some embodiments, the computer may be further configured to use the device interface to transition from being connected to the second device to being connected to the display device by terminating the connection with the second device and establishing the connection with the display device. In some embodiments, the computer may be further configured to use the device interface to transition from being connected to the display device to being connected to the second device by terminating the connection with the display device and establishing the connection with the second device.

In some embodiments, the computer may be further configured to use the device interface to establish the connection with the display device by conveying one or more advertising packets and waiting for the display device to connect to the transceiver. In some embodiments, the computer may be further configured to use the device interface to establish the connection with the second device by conveying one or more advertising packets and waiting for the second device to connect to the transceiver. In some embodiments, the computer may be further configured to use the device interface to establish the connection with the second device by receiving one or more advertising packets from the second device and connecting to the second device. In some embodiments, the two or more devices may further include a third device, and the computer may be further configured to use the device interface to establish a connection with the third device while being connected with no other device of the two or more devices and convey or receive third information to or from the third device while connected with the third device. In some embodiments, the computer may be further configured to calculate an analyte level using at least the received measurement information, and the first information includes the calculated analyte level. In some embodiments, the first information may include the measurement information.

Still another aspect of the invention may provide a display device including a transceiver interface, a user interface, and a computer. The transceiver interface may be configured to receive first information from a transceiver. The computer may include a non-transitory memory and a processor. The computer may be configured to (i) use the transceiver interface to establish a connection with the transceiver, (ii) use the transceiver interface to receive an analyte level from the transceiver while connected with the transceiver, (iii) cause the user interface to display an analyte level based on at least the first information, and (iv) use the transceiver interface to terminate the connection with the transceiver if any of one or more disconnection events occur.

In some embodiments, the computer may be further configured to execute a mobile medical application (MMA), and the one or more disconnection events may include the MMA transitioning from being run in the foreground to running in the background. In some embodiments, the one or more disconnection events may include detecting an available connection with a second device. In some embodiments, the computer may be further configured to use the transceiver interface to establish the connection with the transceiver by receiving one or more advertising packets from the transceiver and connecting to the transceiver. In some embodiments, the displayed analyte level is included in the first information. In some embodiments, the first information may include measurement information, and the computer may be further configured to calculate the displayed analyte level using at least the measurement information.

Yet another aspect of the invention may provide a method of using an analyte system including an analyte sensor, a transceiver, and two or more devices including a display device and a second device. The method may include using the transceiver to receive measurement information from the analyte sensor. The method may include using the transceiver to establish a connection with the display device while being connected with no other device of the two or more devices. The method may include using the transceiver to convey first information to the display device while connected with the display device. The method may include using the display device to receive the first information from the transceiver and display an analyte level based on at least the first information. The method may include using the transceiver to establish a connection with the second device while being connected with no other device of the two or more devices. The method may include using the transceiver to convey or receive second information to or from the second device while connected with the second device. The method may include using the second device to receive or convey the second information from or to the transceiver.

In some embodiments, the method may further include using the display device to terminate the connection with the transceiver if any of one or more disconnection events occur. In some embodiments, the method may further include using the display device to execute a mobile medical application (MMA), and the one or more disconnection events may include the MMA transitioning from being run in the foreground to running in the background. In some embodiments, the one or more disconnection events may include the display device detecting an available connection with the second device. In some embodiments, the method may further include: using the display device to terminate the connection between the transceiver and the display device, and using the transceiver to establish the connection with the second device in response to the display device terminating the connection with the transceiver.

In some embodiments, the method may further include: using the transceiver to store an identification of each of the two or more devices in a memory of the transceiver, and using the transceiver to transition between connections with the identified two or more devices at scheduled intervals. In some embodiments, the method may further include using the transceiver to transition from being connected to the display device to being connected to the second device and from being connected to the second device to being connected to the display device at scheduled intervals. In some embodiments, the method may further include using the transceiver to transition from being connected to the second device to being connected to the display device by terminating the connection with the second device and establishing the connection with the display device. In some embodiments, the method may further include using the transceiver to transition from being connected to the display device to being connected to the second device by terminating the connection with the display device and establishing the connection with the second device.

In some embodiments, the method may further include using the transceiver to establish the connection with the display device by conveying one or more advertising packets and waiting for the display device to connect to the transceiver. In some embodiments, the method may further include using the transceiver to establish the connection with the second device by conveying one or more advertising packets and waiting for the second device to connect to the transceiver. In some embodiments, the method may further include using the transceiver to establish the connection with the second device by receiving one or more advertising packets from the second device and connecting to the second device.

In some embodiments, the two or more devices may further include a third device, and the method may further include using the transceiver to establish a connection with the third device while being connected with no other device of the two or more devices and convey or receive third information to or from the third device while connected with the third device. In some embodiments, the method may further include using the transceiver to calculate an analyte level using at least the measurement information, the first information may include the calculated analyte level, and the analyte level displayed by the display device may be the calculated analyte level. In some embodiments, the first information may include the measurement information, and the display device may be further configured to calculate the displayed analyte level using at least the measurement information.

Still another aspect of the invention may provide an analyte monitoring system including an analyte sensor, two or more devices including a display device and a second device, and a transceiver. The transceiver may be configured to (i) receive measurement information from the analyte sensor, (ii) establish a connection with the display device with the transceiver configured as a slave device and the display device configured as a master device, (iii) convey first information to the display device while connected with the display device, (iv) establish a connection with the second device with the transceiver configured as a master device and the second device configured as a slave device, and (v) convey or receive second information to or from the second device while connected with the second device. The display device may be configured to (i) receive first information from the transceiver and (ii) display an analyte level based on at least the first information, and the second device may be configured to receive or convey the second information from or to the transceiver.

In some embodiments, the two or more devices may further include a third device, the transceiver may be further configured to establish a connection with the third device while being connected with the second device, the third device may be configured as a slave device, and the transceiver may be further configured to convey or receive third information to or from the third device while connected with the second and third devices.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
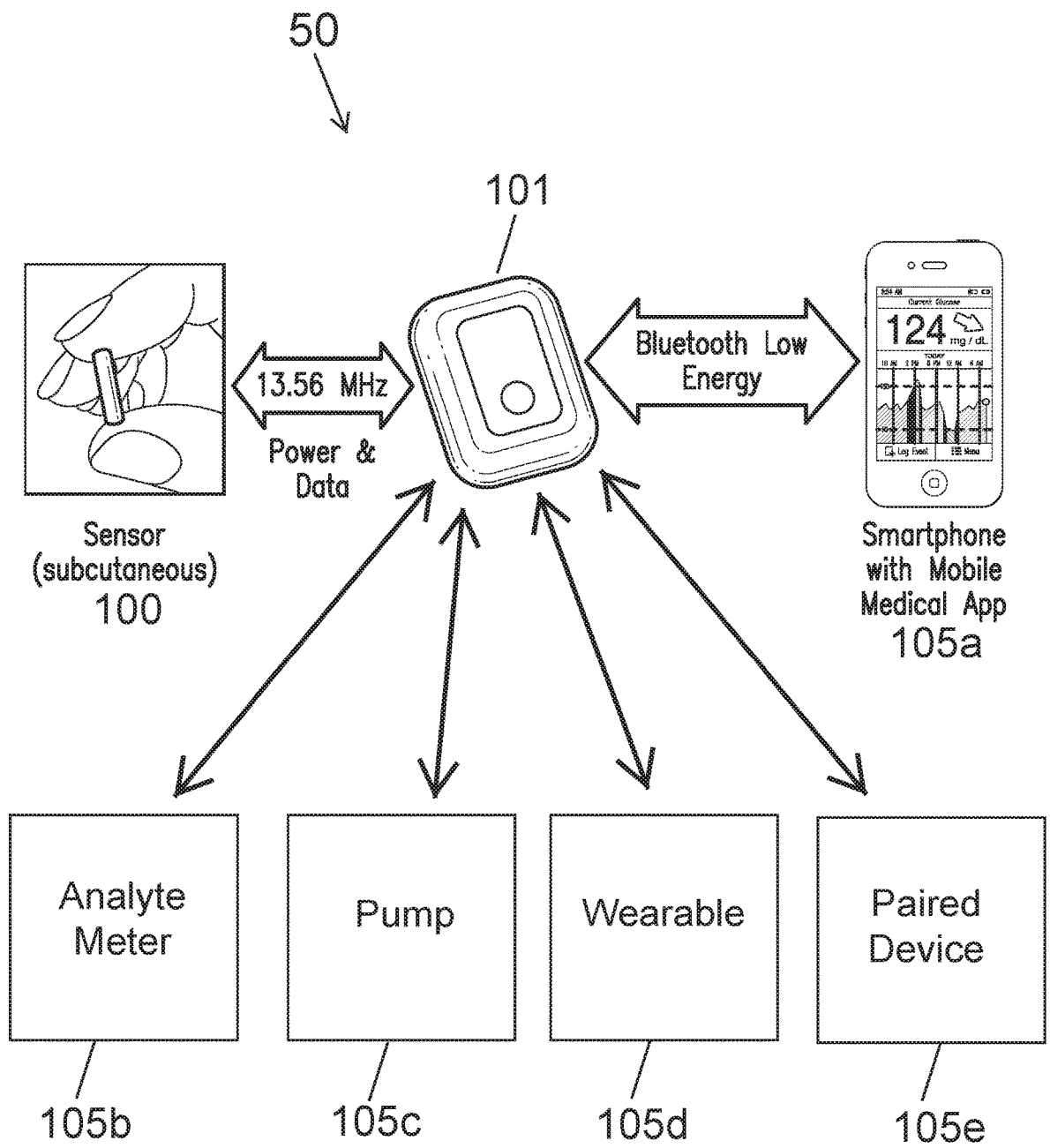
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and two or more devices 105. In some embodiments, the two or more devices 105 may include one or more display devices 105a, one or more analyte meters 105b, one or more infusion pumps 105c, one or more wearables 105d, and/or one or more additional devices 105e. In some embodiments, the two or more devices 105 may include at least a display device 105a and a second device, which may be an analyte meter 105b, an infusion pump 105c, a wearable 105d, or another device 105e. In some embodiments, the two or more devices 105 may additionally include a third device, which may be an analyte meter 105b, an infusion pump 105c, a wearable 105d, or another device 105e.

In some embodiments, the display device 105a may be, for example and without limitation, a smartphone or a tablet. In some embodiments, the display device 105a may execute a mobile medical application (MMA). In some embodiments, the analyte meter 105b may be, for example and without limitation, a blood glucose meter. In some embodiments, the infusion pump 105c may be, for example and without limitation, an insulin pump. In some embodiments, the wearable 105d may be, for example and without limitation, a smart watch or Fitbit. In some embodiments, the device 105e may be, for example and without limitation, a vehicle (e.g., a Bluetooth® enabled car).

In some embodiments, the sensor 100 may be small, fully subcutaneously implantable sensor. However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may communicate with the sensor to initiate and receive one or more sensor measurements via a wireless connection (e.g., via near field communication (NFC)) or a wired connection. In some embodiments, the sensor measurements may include one or more light measurements and/or one or more temperature measurements. In some embodiments, the one or more sensor measurements may be indicative of an amount or concentration of an analyte in a medium (e.g., interstitial fluid) of a living animal (e.g., a living human). In some embodiments, the transceiver 101 may calculate one or more analyte levels (e.g., analyte concentrations) using at least the received sensor measurements. In some embodiments, the transceiver 101 may convey and/or receive information wirelessly (e.g., via a Bluetooth® communication standard such as, for example and without limitation Bluetooth® Low Energy (BLE)) to and/or from the devices 105. For example, in some embodiments, the transceiver 101 may convey information (e.g., one or more analyte levels) to a mobile medical application (MMA) running on a display device 105a (e.g., a smartphone or tablet). In some embodiments, the transceiver 101 may additionally or alternatively convey and/or receive information to and/or from the devices 105 using a wired connection (e.g., using a Universal Serial Bus (USB) port). In some embodiments, the analyte monitoring system 50 may include a web interface for communicating with a data management system for plotting and sharing of the analyte information.

Figure 2:
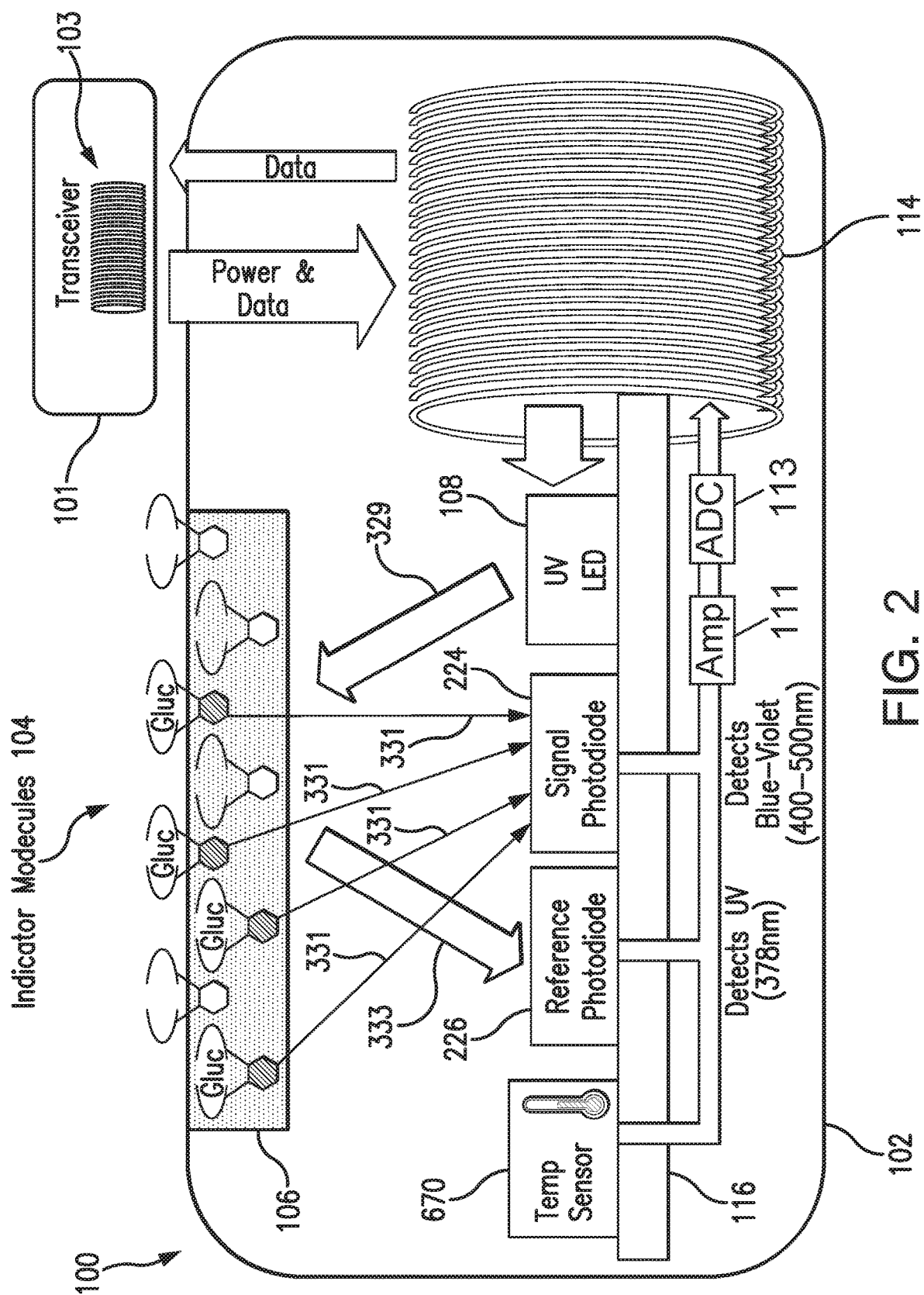
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in some embodiments, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in some embodiments, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some embodiments, as illustrated in FIG. 2, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some embodiments, one or more of the photodetectors (e.g., photodetector 226) may be sensitive to excitation light 329 that is reflected from the analyte indicator element 106 as reflection light 333. In some embodiments, one or more of the photodetectors may be covered by one or more filters (e.g., one or more bandpass filters) that allow only a certain subset of wavelengths of light to pass through (e.g., a subset of wavelengths corresponding to emission light 331 or a subset of wavelengths corresponding to reflection light 333) and reflect or absorb the remaining wavelengths. In some embodiments, the sensor 100 may include a temperature transducer 670. In some embodiments, the sensor 100 may include a drug-eluting polymer matrix that disperses one or more therapeutic agents (e.g., an anti-inflammatory drug).

In some embodiments, the outputs of one or more of the photodetectors 224, 226 and the temperature transducer 670 may be amplified by an amplifier 111. In some embodiments, the amplifier 111 may be a comparator that receives analog light measurement signals from the photodetectors 224, 226 and output an analog light difference measurement signal indicative of the difference between the received analog light measurement signals. In some embodiments, the amplifier 111 may be a transimpedance amplifier. However, in some alternative embodiments, a different amplifier may be used. In some embodiments, the outputs of one or more of the photodetectors 224, 226, the temperature transducer 670, and the amplifier 111 may be converted to a digital signal by an analog-to-digital converter (ADC) 113.

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface. In some embodiments where the sensor 100 includes an antenna (e.g., inductive element 114), the transceiver interface may include the antenna (e.g., inductive element 114) of sensor 100. In some of the transcutaneous embodiments where there exists a wired connection between the sensor 100 and the transceiver 101, the transceiver interface may include the wired connection.

Figure 3:
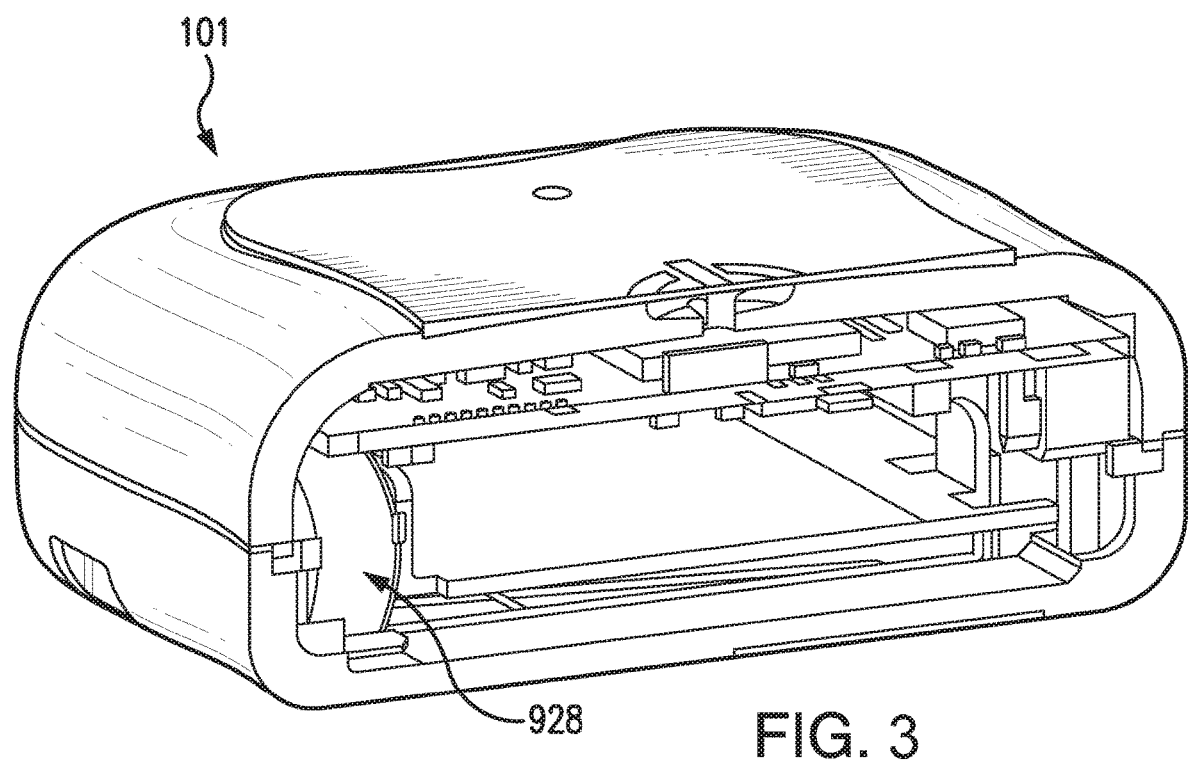
FIG. 3 is cross-sectional, perspective view of a transceiver embodying aspects of the invention.
Figure 4:
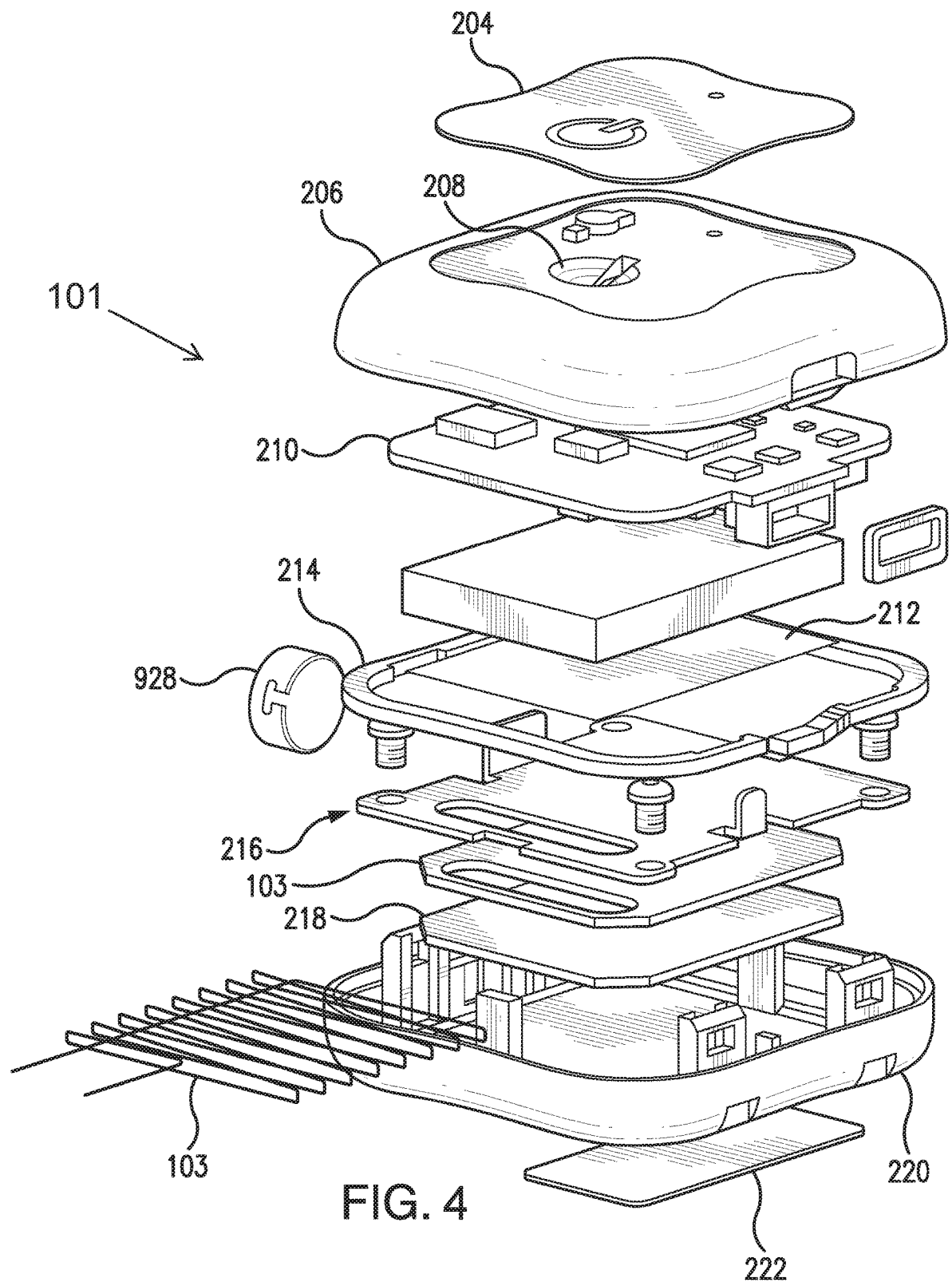
FIG. 4 is an exploded, perspective view of a transceiver embodying aspects of the invention.

FIGS. 3 and 4 are cross-sectional and exploded views, respectively, of one embodiment of the transceiver 101, which may be included in the analyte monitoring system illustrated in FIG. 1. As illustrated in FIG. 4, in some embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some embodiments, the vibration motor 928 may be attached to the front housing 206 or back housing 220 such that the battery 212 does not dampen the vibration of vibration motor 928. In some embodiments, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the transceiver 101 may be suitable for placement, for example, on an abdomen area, upper-arm, wrist, or thigh of a patient body. In some embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
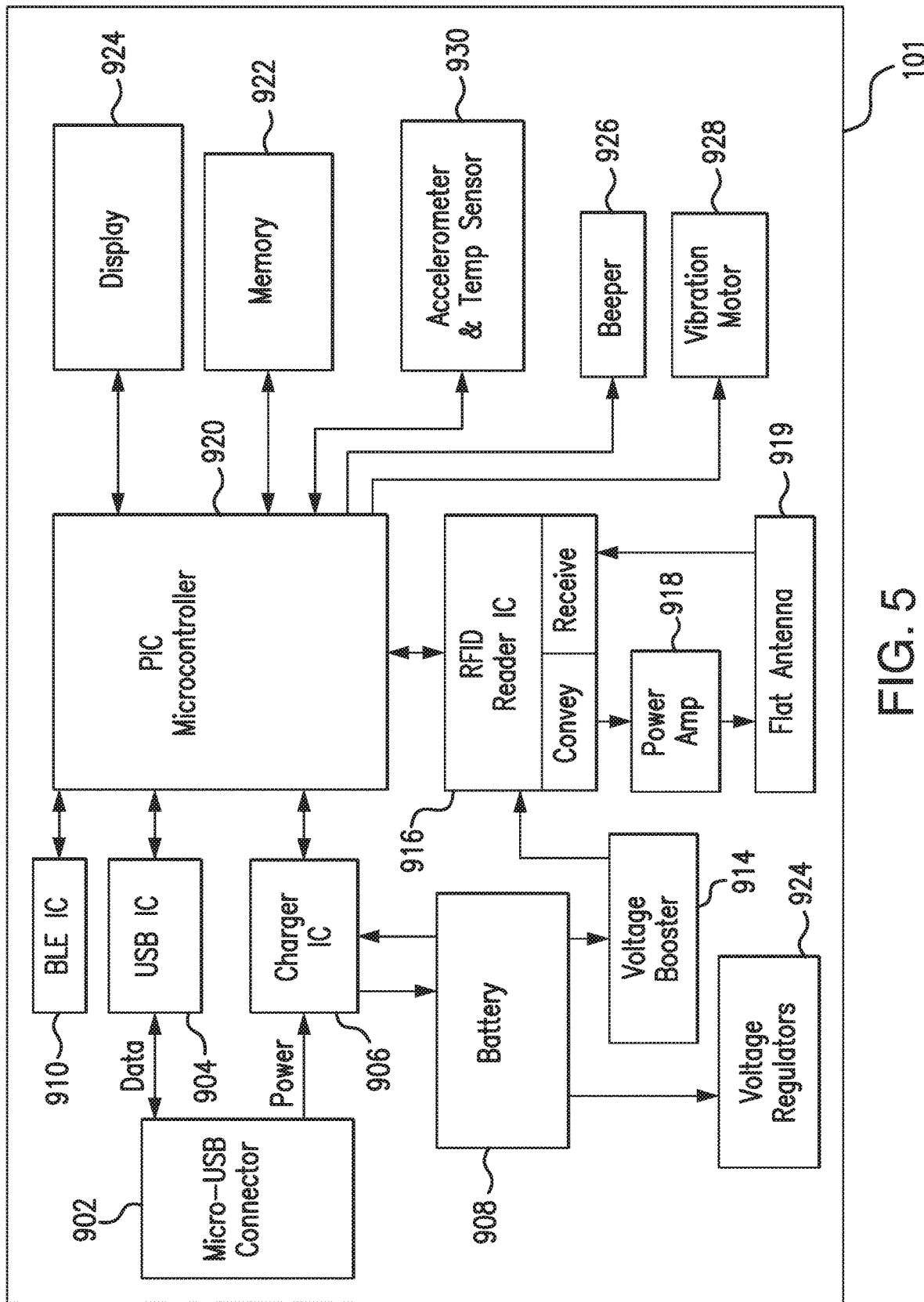
FIG. 5 is a schematic view illustrating a transceiver embodying aspects of the present invention.

FIG. 5 is a schematic view of an external transceiver 101 according to some embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer) or a device 105 (e.g., a display device 105a, an analyte meter 105b, an infusion pump 105c, a wearable 105d, or another device 105e).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer) or one or more devices 105. In some embodiments, the wireless communication IC 910 may employ one or more wireless communication standards to wirelessly transmit data. The wireless communication standard employed may be any suitable wireless communication standard, such as an ANT standard, a Bluetooth® standard, or a Bluetooth® Low Energy (BLE) standard (e.g., BLE 4.0). In some embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth® antenna). In some embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a device interface, which may enable communication by the transceiver 101 with one or more devices 105 (e.g., one or more display devices 105a, one or more analyte meters 105b, one or more infusion pumps 105c, one or more wearables 105d, and/or one or more additional devices 105e). In some embodiments, the device interface may include the antenna of the wireless communication IC 910 and/or the connector 902. In some embodiments, the device interface may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some embodiments, the sensor 100 and transceiver 101 may communicate using near field communication (NFC) (e.g., at a frequency of 13.56 MHz). In the illustrated embodiment, the inductive element 103 is a flat antenna 919. In some embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a processor 920 and a memory 922 (e.g., Flash memory). In some embodiments, the memory 922 may be non-volatile and/or capable of being electronically erased and/or rewritten. In some embodiments, the processor 920 may be, for example and without limitation, a peripheral interface controller (PIC) microcontroller. In some embodiments, the processor 920 may control the overall operation of the transceiver 101. For example, the processor 920 may control the connector IC 904 or wireless communication IC 910 to transmit data via wired or wireless communication and/or control the RFID reader IC 916 to convey data via the inductive element 103. The processor 920 may also control processing of data received via the inductive element 103, connector 902, or wireless communication IC 910.

In some embodiments, the transceiver 101 may include a sensor interface, which may enable communication by the transceiver 101 with a sensor 100. In some embodiments, the sensor interface may include the inductive element 103. In some embodiments, the sensor interface may additionally include the RFID reader IC 916 and/or the power amplifier 918. However, in some alternative embodiments where there exists a wired connection between the sensor 100 and the transceiver 101 (e.g., transcutaneous embodiments), the sensor interface may include the wired connection.

In some embodiments, the transceiver 101 may include a display 924 (e.g., liquid crystal display and/or one or more light emitting diodes), which the processor 920 may control to display data (e.g., analyte levels). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor that may be used in the processing performed by the processor 920.

In some embodiments, the transceiver 101 may be a body-worn transceiver that is a rechargeable, external device worn over the sensor implantation or insertion site. In some embodiment, the transceiver 101 may supply power to the proximate sensor 100. In some embodiments, power may be supplied to the sensor 100 through an inductive link (e.g., an inductive link of 13.56 MHz). However, it is not required that the sensor 100 receive power from the transceiver 101 (e.g., in the case of a battery-powered sensor). In some embodiments, the transceiver 101 may be placed using an adhesive patch or a specially designed strap or belt. The external transceiver 101 may read measured analyte data from a subcutaneous sensor 100 (e.g., up to a depth of 2 cm or more).

In some embodiments, the transceiver 100 may receive sensor data (e.g., measurement information such as, for example and without limitation, light measurements and/or temperature measurements) from the sensor 100. In some embodiments, the transceiver 101 may periodically (e.g., every 2, 5, or 10 minutes) read sensor data. However, this is not required, and, in some alternative embodiments, the transceiver 101 may read sensor data on-demand (e.g., by swiping or bringing the transceiver 101 in proximity to the sensor 101). In some embodiments, the transceiver 101 may calculate analyte levels (e.g., analyte concentrations) using at least the received sensor data. In some embodiments, the transceiver 101 may calculate analyte level rate of change information (e.g., analyte concentration trends) using the calculated analyte levels and/or the received sensor data. In some embodiments, the transceiver 101 may transmit one or more of the calculated analyte levels and the calculated analyte level rate of change information to a display device 105a (see FIG. 1). In some embodiments, the transceiver 101 may also determine if an alert and/or alarm condition exists and generate one or more alerts or alarms, which may be signaled to the user (e.g., through vibration by vibration motor 928 and/or an LED of the transceiver's display 924 and/or a user interface of a display device 105a).

In some embodiments, the transceiver 101 may convey information (e.g., one or more of sensor data, calculated analyte levels, calculated analyte level rates of change, alerts, alarms, and notifications) to one or more display devices 105a (e.g., via Bluetooth® Low Energy with Advanced Encryption Standard (AES)-Counter CBC-MAC (CCM) encryption) for display by a mobile medical application (MMA) being executed by the display device 105a. In some embodiments, the MMA may generate alarms, alerts, and/or notifications (in addition to or as an alternative to receiving alerts, alarms, and/or notifications from the transceiver 101). In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 50 may receive raw signals indicative of an amount or concentration of an analyte in proximity to the analyte indicator element 106 of the analyte sensor 100. In some embodiments, the transceiver 101 may receive the raw signals from the sensor 100 periodically (e.g., every 5, 10, or 20 minutes). In some embodiments, the raw signals may include one or more analyte measurements (e.g., one or more measurements indicative of the level of emission light 331 from the indicator molecules 104 as measured by the photodetector 224) and/or one or more temperature measurements (e.g., as measured by the temperature transducer 670). In some embodiments, the transceiver 101 may use the received raw signals to calculate analyte levels. In some embodiments, the transceiver 100 may store one or more calculated analyte levels (e.g., in memory 922). In some embodiments, the transceiver 100 may convey one or more calculated analyte levels to the display device 105.

In some embodiments, as noted above, the transceiver 101 may calculate one or more of analyte levels and analyte level rates of change and/or may generate one or more of alerts, alarms, and notifications. However, it is not required that the transceiver 101 perform the calculations and/or generate the alerts, alarms, and notifications itself, and, in some alternative embodiments, the transceiver 101 may instead convey/relay the measurement information received from the sensor 100 to another device 105 (e.g., display device 105a) for calculation of one or more of analyte levels and analyte level rates of change and/or generation one or more of alerts, alarms, and notifications (e.g., by a mobile medical application executing on the display device 105a). In some alternative embodiments, the transceiver 101 may calculate analyte levels using at least sensor data received from the sensor 100 and convey the calculated analyte levels to the display device 105a, and the display device 105a may calculate analyte level rates of change using at least the received analyte levels and/or generate one or more of alerts, alarms, and notifications using at least the received analyte levels.

Figure 6:
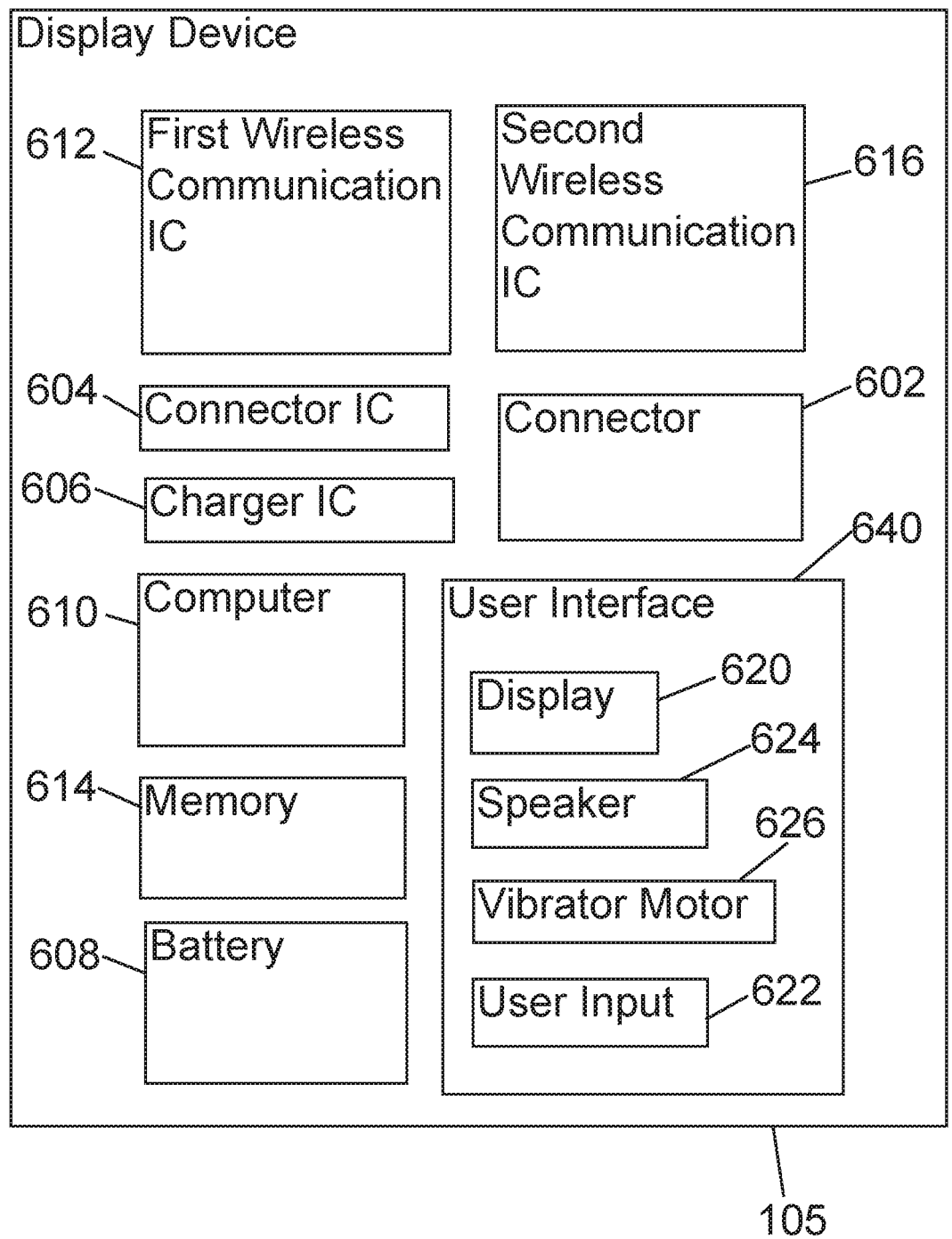
FIG. 6 illustrates a block diagram of a display device of the analyte monitoring system according to some embodiments.

FIG. 6 is a block diagram of one embodiment of the display device 105a of the analyte monitoring system 50. As shown in FIG. 6, in some embodiments, the display device 105a may include one or more of a connector 602, a connector integrated circuit (IC) 604, a charger IC 606, a battery 608, a computer 610, a first wireless communication IC 612, a memory 614, a second wireless communication IC 616, and a user interface 640.

In some embodiments in which the display device 105a includes the connector 602, the connector 602 may be, for example and without limitation, a Micro-Universal Serial Bus (USB) connector. The connector 602 may enable a wired connection to an external device, such as a personal computer or transceiver 101 (e.g., via the connector 902 of the transceiver 101). The display device 105a may exchange data to and from the external device through the connector 602 and/or may receive power through the connector 602. In some embodiments, the connector IC 604 may be, for example and without limitation, a USB-IC, which may control transmission and receipt of data through the connector 602.

In some embodiments in which the display device 105a includes the charger IC 606, the charger IC 606 may receive power via the connector 602 and charge the battery 608. In some embodiments, the battery 608 may be, for example and without limitation, a lithium-polymer battery. In some embodiments, the battery 608 may be rechargeable, may have a short recharge duration, and/or may have a small size.

In some embodiments, the display device 105a may include one or more connectors and/or one or more connector ICs in addition to (or as an alternative to) connector 602 and connector IC 604. For example, in some alternative embodiments, the display device 105 may include a spring-based connector (e.g., Pogo pin connector) in addition to (or as an alternative to) connector 602, and the display device 105a may use a connection established via the spring-based connector for wired communication to a personal computer or the transceiver 101 and/or to receive power, which may be used, for example, to charge the battery 608.

In some embodiments in which the display device 105a includes the first wireless communication IC 612, the first wireless communication IC 612 may enable wireless communication with one or more external devices, such as, for example, one or more personal computers, one or more transceivers 101, and/or one or more other devices 105. In some embodiments, the first wireless communication IC 612 may employ one or more wireless communication standards to wirelessly transmit data. The wireless communication standard employed may be any suitable wireless communication standard, such as an ANT standard, a Bluetooth® standard, or a Bluetooth® Low Energy (BLE) standard (e.g., BLE 4.0). In some embodiments, the first wireless communication IC 612 may be configured to wirelessly transmit data at a frequency greater than 1 gigahertz (e.g., 2.4 or 5 GHz). In some embodiments, the first wireless communication IC 612 may include an antenna (e.g., a Bluetooth® antenna). In some embodiments, the antenna of the first wireless communication IC 612 may be entirely contained within a housing of the display device 105a. However, this is not required, and, in alternative embodiments, all or a portion of the antenna of the first wireless communication IC 612 may be external to the display device housing.

In some embodiments, the display device 105a may include a transceiver interface, which may enable communication by the display device 105a with one or more transceivers 101 and/or one or more other devices 105. In some embodiments, the transceiver interface may include the antenna of the first wireless communication IC 612 and/or the connector 602. In some embodiments, the transceiver interface may additionally or alternatively include the first wireless communication IC 612 and/or the connector IC 604.

In some embodiments in which the display device 105*a* includes the second wireless communication IC 616, the second wireless communication IC 616 may enable the display device 105*a* to communicate with one or more remote devices (e.g., smartphones, servers, and/or personal computers) via wireless local area networks (e.g., Wi-Fi), cellular networks, and/or the Internet. In some embodiments, the second wireless communication IC 616 may employ one or more wireless communication standards to wirelessly transmit data. In some embodiments, the second wireless communication IC 616 may include one or more antennas (e.g., a Wi-Fi antenna and/or one or more cellular antennas). In some embodiments, the one or more antennas of the second wireless communication IC 616 may be entirely contained within a housing of the display device 105*a*. However, this is not required, and, in alternative embodiments, all or a portion of the one or more antennas of the second wireless communication IC 616 may be external to the display device housing.

In some embodiments in which the display device 105*a* includes the memory 614, the memory 614 may be non-volatile and/or capable of being electronically erased and/or rewritten. In some embodiments, the memory 614 may be, for example and without limitations a Flash memory.

In some embodiments in which the display device 105*a* includes the computer 610, the computer 610 may control the overall operation of the display device 105*a*. For example, the computer 610 may control the connector IC 604, the first wireless communication IC 612, and/or the second wireless communication IC 616 to transmit data via wired or wireless communication. The computer 610 may additionally or alternatively control processing of received data (e.g., analyte monitoring data received from the transceiver 101).

In some embodiments in which the display device 105*a* includes the user interface 640, the user interface 640 may include one or more of a display 620 and a user input 622. In some embodiments, the display 620 may be a liquid crystal display (LCD) and/or light emitting diode (LED) display. In some embodiments, the user input 622 may include one or more buttons, a keyboard, a keypad, and/or a touchscreen. In some embodiments, the computer 610 may control the display 620 to display data (e.g., analyte levels, analyte level rate of change information, alerts, alarms, and/or notifications). In some embodiments, the user interface 640 may include one or more of a speaker 624 (e.g., a beeper) and a vibration motor 626, which may be activated, for example, in the event that a condition (e.g., a hypoglycemic or hyperglycemic condition) is met.

In some embodiments, the computer 610 may execute a mobile medical application (MMA). In some embodiments, the display device 105*a* may receive analyte monitoring data from the transceiver 101. In some embodiments, the received analyte monitoring data may include one or more analyte levels, one or more analyte level rates of change, and/or one or more sensor measurements. In some embodiments, the received analyte monitoring data may additionally or alternatively include alarms, alerts, and/or notifications. In some embodiments, the MMA may display some or all of the received analyte monitoring data on the display 620 of the display device 105*a*. In some alternative embodiments, the received analyte monitoring data may include one or more sensor measurements and does not include analyte levels, and the display device 105*a* may calculate one or more analyte levels using the one or more sensors measurements. In some alternative embodiments, the received analyte monitoring data may include one or more analyte levels but does not include analyte level rates of change, and the display device 105*a* may calculate one or more analyte level rates of change using the one or more analyte levels. In some alternative embodiments, the display device 105*a* may calculate one or more analyte levels and calculate one or more analyte level rates of change using at least the one or more analyte levels calculated by the display device 105*a*.

In some embodiments, the analyte monitoring system 50 may calibrate the conversion of raw sensor measurements to analyte levels (e.g., analyte concentrations). In some embodiments, the calibration may be performed approximately periodically (e.g., every 12 or 24 hours). In some embodiments, the calibration may be performed using one or more reference measurements (e.g., one or more self-monitoring blood glucose (SHBG) measurements). In some embodiments, one or more reference measurements may be entered into the analyte monitoring system 50 using the user interface 640 of the display device 105*a*. In some embodiments, the display device 105*a* may convey one or more references measurements to the transceiver 101, and the transceiver 101 may use the one or more received reference measurements to perform the calibration. In some alternative embodiments (e.g., embodiments in which the display device 105*a* calculates one or more analyte levels), the display device 105 may use the one or more received reference measurements to perform the calibration. In some embodiments, the transceiver 101 may additionally or alternatively receive one or more reference measurements from an analyte meter 105*b*.

Figure 7:
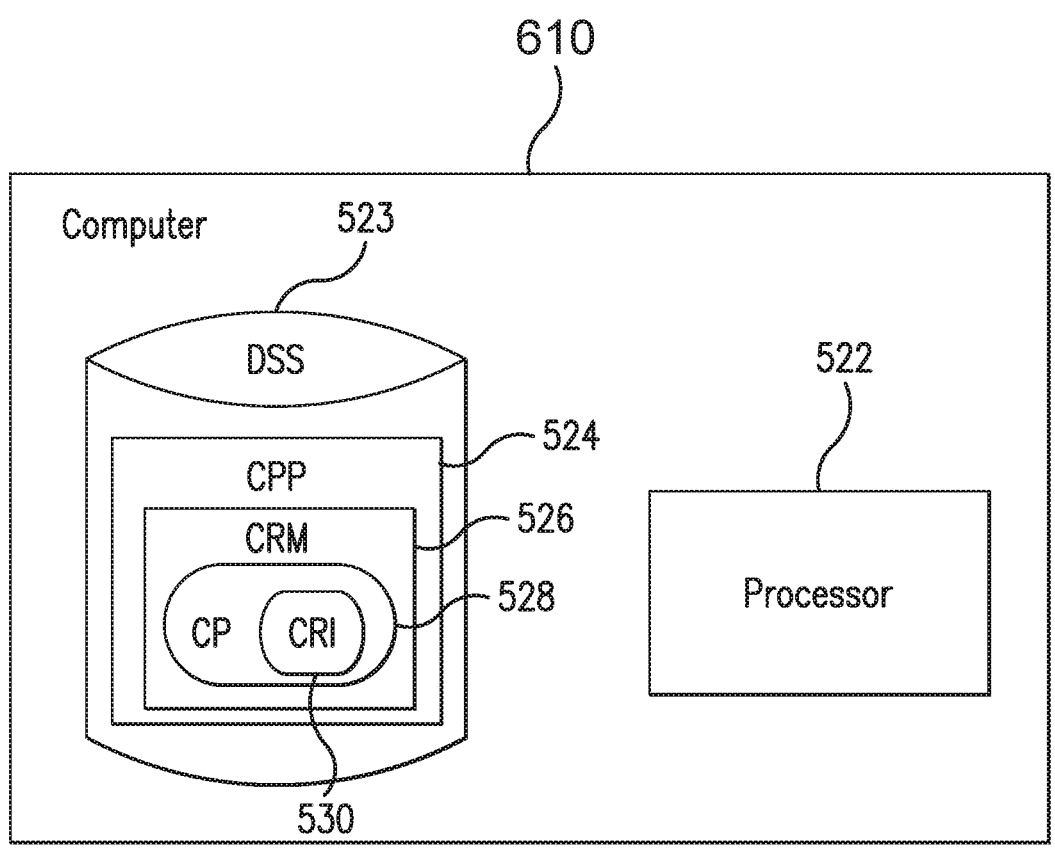
FIG. 7 illustrates a block diagram of a computer of the display device of the analyte monitoring system according to some embodiments.

FIG. 7 is a block diagram of one embodiment of the computer 610 of the display device 105*a* of the analyte monitoring system 50. As shown in FIG. 3, in some embodiments, the computer 610 may include one or more processors 522 (e.g., a general purpose microprocessor) and/or one or more circuits, such as an application specific integrated circuit (ASIC), field-programmable gate arrays (FPGAs), a logic circuit, and the like. In some embodiments, the computer 610 may include a data storage system (DSS) 523. The DSS 523 may include one or more non-volatile storage devices and/or one or more volatile storage devices (e.g., random access memory (RAM)). In embodiments where the computer 610 includes a processor 522, the DSS 523 may include a computer program product (CPP) 524. CPP 524 may include or be a computer readable medium (CRM) 526. The CRM 526 may store a computer program (CP) 528 comprising computer readable instructions (CRI) 530. In some embodiments, the CRM 526 may store, among other programs, the MMA, and the CRI 530 may include one or more instructions of the MMA. The CRM 526 may be a non-transitory computer readable medium, such as, but not limited to, magnetic media (e.g., a hard disk), optical media (e.g., a DVD), solid state devices (e.g., random access memory (RAM) or flash memory), and the like. In some embodiments, the CRI 530 of computer program 528 may be configured such that when executed by processor 522, the CRI 530 causes the computer 610 to perform steps described below (e.g., steps described below with reference to the MMA). In other embodiments, the computer 610 may be configured to perform steps described herein without the need for a computer program. That is, for example, the computer 610 may consist merely of one or more ASICs.

Hence, the features of the embodiments described herein may be implemented in hardware and/or software.

In some embodiments in which the user interface 640 of the display device 105*a* includes the display 618, the MMA may cause the display device 105 to provide a series of graphical control elements or widgets in the user interface 640, such as a graphical user interface (GUI), shown on the display 618. The MMA may, for example and without limitation, cause the display device 105 to display analyte related information in a GUI such as, but not limited to: one or more of analyte information, current analyte levels, past analyte levels, predicted analyte levels, user notifications, analyte status alerts and alarms, trend graphs, analyte level rate of change or trend arrows, and user-entered events. In some embodiments, the MMA may provide one or more graphical control elements that may allow a user to manipulate aspects of the one or more display screens. Although aspects of the MMA are illustrated and described in the context of glucose monitoring system embodiments, this is not required, and, in some alternative embodiments, the MMA may be employed in other types of analyte monitoring systems.

In some embodiments where the display device 105*a* communicates with a transceiver 101, which in turn obtains sensor measurement data from the analyte sensor 100, the MMA may cause the display device 105 to receive and display one or more of analyte data, trends, graphs, alarms, and alerts from the transceiver 101. In some embodiments, the MMA may store analyte level history and statistics for a patient on the display device 105 (e.g., in memory 614 and/or DSS 533) and/or in a remote data storage system.

In some embodiments, a user of the display device 105*a*, which may be the same or different individual as patient, may initiate the download of the MMA from a central repository over a wireless cellular network or packet-switched network, such as the Internet. Different versions of the MMA may be provided to work with different commercial operating systems, such as the Android OS or Apple OS running on commercial smart phones, tablets, and the like. For example, where display device 105*a* is an Apple iPhone, the user may cause the display device 105 to access the Apple iTunes store to download a MMA compatible with the Apple OS, whereas where the display device 105*a* is an Android mobile device, the user may cause the display device 105*a* to access the Android App Store to download a MMA compatible with the Android OS.

Figure 8:
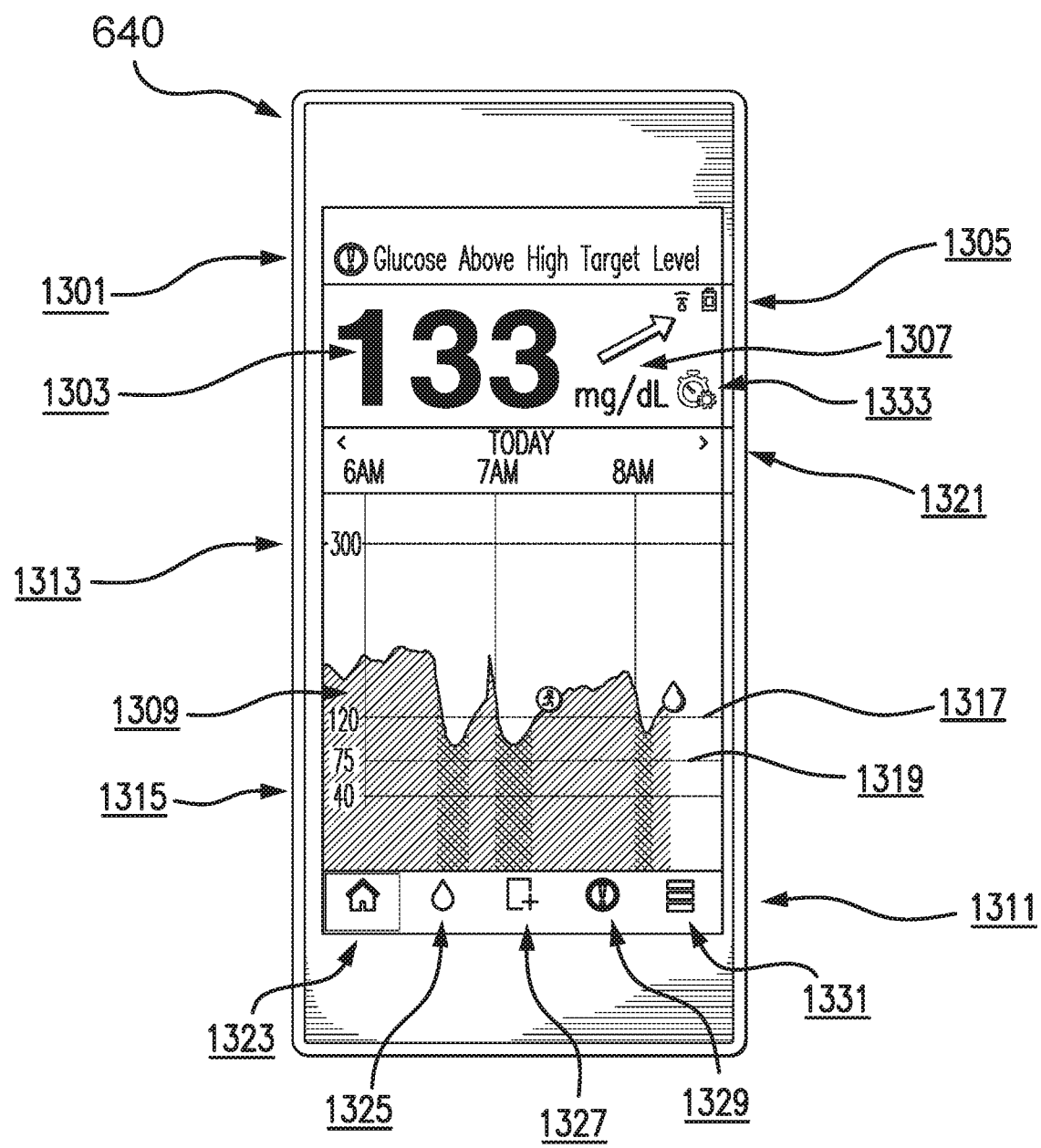
FIG. 8 illustrates a non-limiting example of a home screen illustrative display of a medical mobile application in accordance with aspects of various embodiments of the present invention.

FIG. 8 is an example of a home screen display of a medical mobile application (MMA) in accordance with aspects of various embodiments of the present invention. According to some embodiments, the workspace display of the MMA may be depicted in a GUI on the display 620 of the display device 105*a*. In some embodiments, the home screen may display one or more of real-time analyte levels received from transceiver 101, rate and direction of analyte level change, graphical trends of analyte levels, alarms or alerts for hypoglycemia or hyperglycemia, and logged events such as, for example and without limitation, meals, exercise, and medications. Table 1 below depicts several informational non-limiting examples of items and features that may be depicted on the home screen.

TABLE 1

| Home Screen | |
|---|---|
| Status bar | Shows the status of user's analyte level |
| Transceiver/ | This is the transceiver being used; the transceiver |

TABLE 1-continued

| Home Screen | |
|---|---|
| Transmitter ID | name can be changed by going to Settings > System |
| Current analyte level | A real-time analyte level reading; this may be updated every 5 minutes |
| Date and time | The current date and time with navigational options, such as scroll left or right to see different dates and times |
| Alarm and Events | Shows an icon when an alert, alarm, or event occurs |
| Bluetooth Connection | Shows the strength of the Bluetooth connection |
| Handheld Device Battery Level | Indicates the battery strength of the handheld device |
| Transmitter/ Transceiver Battery Level | Indicates the battery strength of the transceiver |
| Transmitter/ Transceiver Connection Status Icon | Shows the strength of the transceiver connection |
| Trend Arrow | Shows the direction a patient's analyte level is trending |
| Unit of Measurement | This is the units for the analyte level value |
| High Analyte Alarm Level | This is the high analyte alarm or alert level set by a user |
| Analyte High Target Level | This is the high analyte target level set by a user |
| Stacked Alerts | Shows when there are several alerts at the same time |
| Analyte Trend Graph | A user can navigate or scroll through the graph to see the trend over time |
| Menu | Navigation to various sections of the MMA, such as: Home   Reports    Settings Calibrate  Share My Data  About Notifications  Placement Guide Event Log  Connect |
| Calibration Point Icon | This icon appears when a calibration is entered |
| Profile Indicator | This indicator may indicate what profile is being applied, such as a normal profile, temporary profile, vacation profile, and the like. |

In some embodiments, as shown in FIG. 8, the home screen may include one or more of a status notification bar 1301, a real-time current analyte level 1303 of a patient, one or more icons 1305, a trend arrow 1307, a historical graph 1309, a profile indicator 1333, and navigation tools 1311. The status notification bar 1301 may depict, for example and without limitation, alarms, alerts, and notifications related to, for example, analyte levels and system statistics and/or status. The one or more icons 1305 may represent the signal strength of the transceiver 101 and/or the battery level of the transceiver 101. The trend arrow 1307 may indicate a rate and/or direction of change in analyte levels of a patient. The historical graph may be, for example and without limitation, a line graph and may indicate trends of analyte levels of a patient. The navigation tools 1311 may allow a user to navigate through different areas or screens of the MMA. The screens may include, for example and without limitation, one or more of Home, Calibrate, Event Log, Notifications, and Menu screens.

In some embodiments, the historical graph 1309 may depict logged events and/or user inputted activities such as meals (nutrition, amount of carbohydrates), exercise (amount of exercise), medication (amount of insulin units), and blood analyte values as icons on positions of the graph corresponding to when such events occurred. In some embodiments, the historical graph 1309 may show one or more of a boundary or indication of a high analyte alarm level 1313, a low analyte alarm level 1315, a high analyte target level 1317, and a low analyte target level 1319. In some embodiments, a user may interact with a time or date range 1321 option via the GUI to adjust the time period of the analyte level displayed on the historical graph 1309. In some embodiments, the date range 1321 may be specified by a user and may bet set to different time periods such as 1, 3, 24 hours, 1, 7, 14, 30, and 60 days, weeks, months, etc. In some embodiments, the line graph 1309 may show high, low, and average analyte levels of a patient for the selected date range 1321. In other embodiments, the line graph 1309 may be a pie chart, log book, modal day, or other depiction of analyte levels of a patient over a selectable date range 1321, any of which may further depict high, low, and average analyte levels of the patient over that date range 1321.

In some embodiments, the trend arrow 1307 may be depicted in five different configurations that signify direction (up, down, neutral) and rate (rapidly, very rapidly slow, slow, very slow, and stable) of analyte change. In some embodiments, the MMA and/or the transceiver 101 may use the last twenty minutes of continuous analyte measurement data received from the sensor 100 and/or calculated analyte levels in the calculation used to determine the orientation of the trend arrow 1307. In some embodiments, there may be times when the trend arrow 1307 may not be displayed due to, for example, there being insufficient sensor values available for the trend calculation. In some embodiments, a trend arrow 1307 displayed in a horizontal orientation (approximately 0° along the horizontal direction of the GUI display) may indicate that the analyte level is changing gradually, such as, for example, at a rate between −1.0 mg/dL and 1.0 mg/dL per minute. In some embodiments, a trend arrow 1307 displayed slightly in the upwards direction (approximately 45° up from the horizontal direction of the GUI display) may indicate that the analyte level is rising moderately, such as, for example, at a rate between 1.0 mg/dL and 2.0 mg/dL per minute. In some embodiments, a trend arrow 1307 displayed slightly in the downwards direction (approximately 45° down from the horizontal direction of the GUI display) may indicate that the analyte level is falling moderately, such as, for example, at a rate between 1.0 mg/dL and 2.0 mg/dL per minute. In some embodiments, a trend arrow 1307 displayed in a vertical direction (approximately 90° up from the horizontal direction of the GUI display) may indicate that the analyte level is rising very rapidly, such as, for example, at a rate more than 2.0 mg/dL per minute. In some embodiments, a trend arrow 1307 displayed in a downwards direction (approximately 90° down from the horizontal direction of the GUI display) may indicate that the analyte level is falling very rapidly, such as, for example, at a rate more than 2.0 mg/dL per minute. In some embodiments, the trend arrow 1307 is different from a predicted analyte alarm or alert. For example, the trend arrow 1307 may indicate rate and direction of change regardless of analyte value, whereas predicted analyte alarms or alerts may indicate reaching a certain analyte level based on current trends. For example, the MMA may cause a predicted low analyte alarm or alert to be displayed in the notification bar 1301 while still displaying a relatively stable trend arrow 1307 (e.g., at 0° or 45° from the horizontal direction of the GUI display).

In some embodiments, the historical line graph 1309 may allow user to quickly review and analyze historical data and/or trend information of a patient's analyte levels over time. In some embodiments, the historical line graph 1309 may include icons or markers along the trend line to reflect alarms, alerts, notifications, and/or any events that were automatically or manually logged by the user into the display device 105 via a GUI display generated by the MMA. Where one or more of such icons or markers are displayed on the historical line graph 1309, a user may select any one of the icons or markers to obtain more information about the item. For example, in response to a selection of a mark on the line graph 1309, the MMA may generate a popup window on the display 620 that provides more information about the mark.

In some embodiments, the historical line graph 1309 may enable a user to quickly review how well a patient is doing against analyte targets and/or alarms or alerts. For example, a user may establish a high analyte alarm level 1313 and/or a low analyte alarm level 1315, as well as a high analyte target level 1317 and/or a low analyte target level 1319. The high analyte alarm level 1313 and/or low analyte alarm level 1315 may be visually depicted over the historical line graph 1309, for example, using a colored dashed line (such as red). Additionally, the high analyte target level 1317 and low analyte target level 1319 may be visually depicted over the historical line graph 1309, for example, using a color dashed line (such as green).

In some embodiments, the colors of the historical line graph 1309 may change depending on an analyte level 1303 status. For example, during the times where the analyte level 1303 was outside of the high analyte alarm level 1313 or low analyte alarm level 1315, then the portion of the line graph 1309 corresponding to those times may be filled in red. As another example, during the times where the analyte level 1303 is between the high analyte target level 1317 and the low analyte target level 1319, then the portion of the line graph 1309 corresponding to those times may be filled in green. As yet another example, during the times where the analyte level 1303 is between an analyte target level 1317, 1319 and a corresponding alarm level 1313, 1315, then the portion of the line graph 1309 may be filled in yellow.

In some embodiments, the line graph 1309 may be displayed with one or more selectable date range icons 1321 that allow a user to change the day/time period corresponding to the line graph 1309 in real-time. For example, a user may select a forwards or backwards selectable option (such as an arrow) or use a swipe or fling gesture that may be recognized by GUI to navigate to a later or earlier time period, respectively, such as a day, month, etc. In some embodiments a user may choose an older graph 1309 to display by tapping the date on the date range 1321 portion of the screen and submitting or entering a desired date and/or time to review. In some embodiments, a user may use one or more gestures that are recognized by the GUI, such as a pinch, zoom, tap, press and hold, or swipe, on graph 1309. For example, a user may pinch the historical line graph 1309 with a thumb and index finger in order to cause the MMA to display different time/dating settings or adjust a time/date setting on the line graph 1309. In some embodiments, a user may tap or press and hold a time event on historical line graph 1309, and in response the MMA may display further detail on the time event, such as a history, reading value, date/time, or association to other events or display a prompt for entry of a time event.

In some embodiments, the MMA may store analyte data 1303 on the display device 105 (e.g., in memory 614 and/or DSS 533) so long as there is available memory space. Additionally or alternatively, the MMA may cause the display device 105 to send a sync request message to store the analyte data 1303 on a remote storage device.

In some embodiments, the MMA may cause the GUI to display navigational tools 1311 that allow a user to navigate to different features and screens provided by the MMA. For example, the navigational tools 1311 may comprise a navigation bar with one or more of a plurality of selectable navigation options 1323, 1325, 1327, 1329, and 1331, such as buttons or icons. As shown in FIG. 8, in some embodiments, the selectable navigation options may allow a user to navigate to one or more of the "Home" screen 1323, a "Calibrate" screen 1325, an "Event Log" screen 1327, a "Notifications" screen 1329, and a "Menu" screen 1331. Upon a user selection of one of the selectable navigation options in the navigation tools area 1311, a new screen corresponding to the selected option may be displayed on a display device by the GUI.

In some embodiments, the analyte monitoring system 50 may generate high and low analyte level alerts to indicate that an analyte level calculated using one or more measurements from the sensor 100 is too high or too low. In some embodiments, the analyte monitoring system 50 may generate a low analyte level alert if the analyte monitoring system 50 determines that a user's analyte level is lower than a lower analyte threshold. In some embodiments, the analyte monitoring system 50 may generate a high analyte level alert if the analyte monitoring system 50 determines that a user's analyte level is higher than an upper analyte threshold. In some embodiments, a user may set one or more of the lower analyte threshold and the upper analyte threshold to customize when the analyte monitoring system 50 will generate high and low analyte level alerts.

In some embodiments, the transceiver 101 may configured to act as a peripheral device, and the display device 105*a* may be configured to act as a central device. In some embodiments, a peripheral may be configured to convey one or more advertising packets and wait for a central to connect to the peripheral. In some embodiments, a central may be configured to scan for advertising packets and to connect to a peripheral from which advertising packets are received. In some embodiments, a central and a peripheral may be referred to as a master and a slave, respectively, while the central and the peripheral are connected. In some embodiments, a central may be able to connect to one or more peripherals at a time. In some embodiments, a peripheral may be able to connect with only one central at a time. In other words, a peripheral that has connected to a central (and is now a slave connected to a master) may not be able to connect to any additional devices while connected to the central. Accordingly, in some embodiments in which the transceiver 101 acts as a peripheral to connect to a display device 105*a* acting as a central, a connection between the display device 105*a* and transceiver 101 (now a master and slave respectively) must be terminated before the transceiver 101 can establish a connection with the one or more of other devices of the two or more devices 105.

In some embodiments, the transceiver 101 may be configured to establish a connection with the display device 105*a* while being connected with no other device of the two or more devices 105. In some embodiments, the transceiver 101 may be configured to terminate any connections with other devices of the two or more devices 105 before establishing the connection with the display device 105*a*.

In some embodiments, the transceiver 101 and display device 105*a* may act as a peripheral and central, respectively, to establish the connection between the transceiver 101 and the display device 105*a* with the transceiver configured as a slave device and the display device configured as a master device. In some embodiments, the transceiver 101 may be configured to establish the connection with the display device 105*a* by conveying one or more advertising packets and waiting for the display device 105*a* to connect to the transceiver 101. In some embodiments, the display device 105*a* may be configured to scan for advertising packets, receive advertising packets from the transceiver 101, and connect to the transceiver 101.

In some embodiments, the transceiver 101 may be configured to convey first information to the display device 105*a* while the transceiver 101 is connected with the display device 105*a*. In some embodiments, the display device 105*a* may be configured to receive the first information from the transceiver 101. In some embodiments, the display device 105*a* may be configured to display an analyte level based on at least the first information.

In some embodiments, the first information may include an analyte level calculated by the transceiver 101 using at least measurement information received from the analyte sensor 100, and the analyte level displayed by the display device 105*a* may be the analyte level calculated by the transceiver 101. In some alternative embodiments, the first information may include measurement information received by the transceiver 101 from the analyte sensor 100, the display device may be configured to calculate the displayed analyte level using at least the measurement information.

In some embodiments, the transceiver 101 may be configured to establish a connection with a second device of the two or more devices 105 while being connected with no other device of the two or more devices 105. In some embodiments, the second device may be the analyte meter 105*b*, infusion pump 105*c*, wearable 105*d*, or another device 105*e*.

In some embodiments, the transceiver 101 may be configured to establish the connection with the second device following termination of the connection with the display device 105*a*. In some embodiments, the display device 105*a* may be configured to terminate the connection with the transceiver 101 if any of one or more disconnection events occur. In some embodiments in which the display device 105*a* executes a mobile medical application (MMA), the one or more disconnection events may include the MMA transitioning from being run in the foreground to running in the background. In some embodiments, the one or more disconnection events may additionally or alternatively include the display device 105*a* detecting an available connection with one or more other devices of the two or more devices 105. In some embodiments, the one or more disconnection events may additionally or alternatively include an amount of time passing since the connection between the transceiver 101 and the display device 105*a* was established. In some embodiments, the transceiver 101 may be configured to terminate the connection with the display device 105*a* (instead of or in addition to the display device 105*a* being configured to terminate the connection).

In some embodiments, the transceiver 101 may be configured to store an identification of each device of the two or more devices 105 in a memory (e.g., memory 922) and transition between connections with the identified two or more devices. For example and without limitation, in one embodiment, the transceiver 101 may store an identification of each of the display device 105*a*, analyte meter 105*b*, infusion pump 105*c*, wearable 105*d*, and other device 105*e*, and transition from being connected to the display device 105*a* to being connected to the analyte meter 105*b* and then to being connected to the infusion pump 105*c* and then to being connected to the wearable 105*d* and then to being connected to the other device 105*e* before transitioning to being connected to the display device 105*a* again. However, this is not required, and some alternative embodiments may use different transition orders (from the display device 105*a* to the analyte meter 105*b* to the display device 105*a* to the infusion pump 105c to the display device 105a to the wearable 105d to the display device 105a and so on). In some embodiments, the transceiver 101 may transition from being connected to one of devices 105 to being connected to another of devices 105 at scheduled intervals. In some embodiments, the transceiver 101 may transition from being connected to one of devices 105 to being connected to another of devices 105 by terminating the connection with the connection with one device and establishing the connection with the other device.

In some embodiments, the transceiver 101 may act as a peripheral to establish a connection between the transceiver 101 and the second device of the two or more devices 105 with the transceiver again configured as a slave device and the other device configured as a master device. In these embodiments, the transceiver 101 may be configured to establish the connection with the second device of the two or more devices 105 by conveying one or more advertising packets and waiting for the second device to connect to the transceiver 101. In these embodiments, the second device may scan for advertising packets, receive advertising packets from the transceiver 101, and connect to the transceiver 101. However, this is not required.

In some alternative embodiments, the transceiver 101 may act as a central to establish a connection between the transceiver 101 and the second device of the two or more devices 105 with the transceiver 101 configured as a master and the second device configured as a slave. In these alternative embodiments, the transceiver 101 may be configured to establish the connection with the second device by scanning for advertising packets, receiving one or more advertising packets from the second device, and connecting to the second device. In these alternative embodiments, the transceiver 101 acting as a central may establish connections with multiple devices of the two or more devices 105 (e.g., two or more of the analyte meter 105b, infusion pump 105c, wearable 105d, and other device 105e) simultaneously.

In some embodiments, the transceiver 101 may be configured to convey or receive second information to or from the second device (e.g., the analyte meter 105b, infusion pump 105c, wearable 105d, or another device 105e) while the transceiver 101 is connected with the second device. In some embodiments, the second device may be configured to receive or convey the second information from or to the transceiver 101.

In some embodiments, after the transceiver 101 has conveyed or received the second information, the connection may be terminated, and the transceiver 101 may establish a connection with the display device 105a or with a third device of the two or more devices 105.

In some embodiments, the transitions between the connections with the different devices of the two or more devices 105 may appear seamless to the user utilizing multiple devices 105. In some embodiments, the transceiver 101 may store all the paired devices in a non-volatile memory (e.g., memory 922) and transitions between the connections at regularly scheduled interval to transmit the information. For example, in one embodiment, if the transceiver 101 is paired with only 1 master device, the transceiver 101 may stay connected with the one master device. However, if the transceiver 101 is paired with two devices (e.g. the display device 105a and a wearable 105d), the transceiver 101 may connect with the display device 105a every $3^{rd}$ minute and with the wearable every $4^{th}$ minute for a 5 minute sampling of analyte information. In some embodiments, the transceiver 101 may continue to maintain the connection with the last connected device.

In some alternative embodiments, a display device 105a configured as a master device could trigger disconnection with the transceiver 101 on certain events that would then free the transceiver 101 acting as a peripheral to connect with a second master device. For example, when the MMA on the display device 105a is in background, the display device 105a may disconnect the transceiver 101, which may cause the transceiver 101 to begin advertising and allow the wearable 105d find the transceiver 101 to connect. When the wearable 105d is out of range, the transceiver 101 may finds the display device 105a to connect and continue to push data. For another example, the display device 105a configured as a master device may trigger disconnection on certain events or conditions, such as for example and without limitation, when display device 105a detects a connection with the wearable 105d in the vicinity. The display device 105a may disconnect from the transceiver 101 and allow the wearable 105d to connect with the transceiver 101.

In some other alternative embodiments, the transceiver 101 may be dynamically configured in master or slave mode based on the paired devices 105. If more than one paired device is stored in the transceiver's non-volatile memory, the transceiver 101 could configure itself as a master to connect with multiple devices 105 (e.g., multiple BLE enabled devices). For example and without limitation, the transceiver 101, when paired with an infusion pump 105c and analyte meter 105b may be configured as a master to pull information from the infusion pump 105c on periodic basis and then disconnect and reconnect with the analyte meter 105b to retrieve analyte data. After the peripheral information is collected, the transceiver 101 may re-configure itself as slave to connect with display device 105a to transmit the data from various peripheral devices (e.g., the infusion pump 105c and analyte meter 105b).

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For instance, in some embodiments, the transceiver 101 may be a smartphone (e.g., an NFC-enabled smartphone). In some embodiments, a smartphone (e.g., an NFC-enabled smartphone) may perform one or more functions of the transceiver 101 and the display device 105. In some embodiments, the smartphone may take the place of both the transceiver 101 and the display device 105. That is, in some alternative embodiments, a smartphone may be used to do one or more of: (i) communicate directly with the sensor 100, (ii) power the sensor 100, (iii) calculate analyte levels using sensor data received from the sensor 100, and (iv) execute the MMA, which displays the analyte levels and/or other analyte monitoring information (e.g., analyte level rate of change or trend information, alerts, alarms, notifications). In some of these alternative embodiments, the smartphone may include the elements illustrated in FIGS. 6 and 7, and the smartphone may additionally include sensor interface elements that enable direct communication with the analyte sensor 100. In some embodiments, the sensor interface may include, for example and without limitation, one or more of an inductive element, an RFID reader IC, a power amplifier, and a voltage booster, such as those described with reference to FIG. 5 above.

What is claimed is:

1. An analyte monitoring system comprising:
an analyte sensor;

two or more devices including a display device and a second device; and a transceiver configured to (i) receive measurement information from the analyte sensor, (ii) establish a connection with the display device only while being connected with no other device of the two or more devices, (iii) convey first information to the display device while connected with the display device, (iv) establish a connection with the second device only while being connected with no other device of the two or more devices, and (v) convey or receive second information to or from the second device while connected with the second device;

wherein the display device is configured to (i) receive the first information from the transceiver and (ii) display an analyte level based on at least the first information, and the second device is configured to receive or convey the second information from or to the transceiver;

wherein the display device is further configured to terminate the connection with the transceiver if any of one or more disconnection events occur, and the one or more disconnection events include the display device detecting an available connection with the second device.

2. The analyte monitoring system of claim 1, wherein the display device executes a mobile medical application (MMA), and the one or more disconnection events include the MMA transitioning from being run in the foreground to running in the background.

3. The analyte monitoring system of claim 1, wherein the transceiver is further configured to establish the connection with the second device in response to the display device terminating the connection with the transceiver.

4. The analyte monitoring system of claim 1, wherein the transceiver comprises a memory, and the transceiver is further configured to store an identification of each of the two or more devices in the memory and transition between connections with the identified two or more devices at scheduled intervals.

5. The analyte monitoring system of claim 1, wherein the transceiver is further configured to transition from being connected to the display device to being connected to the second device and from being connected to the second device to being connected to the display device at scheduled intervals.

6. The analyte monitoring system of claim 5, wherein the transceiver is further configured to transition from being connected to the second device to being connected to the display device by terminating the connection with the second device and establishing the connection with the display device.

7. The analyte monitoring system of claim 5, wherein the transceiver is further configured to transition from being connected to the display device to being connected to the second device by terminating the connection with the display device and establishing the connection with the second device.

8. The analyte monitoring system of claim 1, wherein the transceiver is further configured to establish the connection with the display device by conveying one or more advertising packets and waiting for the display device to connect to the transceiver.

9. The analyte monitoring system of claim 1, wherein the transceiver further is configured to establish the connection with the second device by conveying one or more advertising packets and waiting for the second device to connect to the transceiver.

10. The analyte monitoring system of claim 1, wherein the transceiver is further configured to establish the connection with the second device by receiving one or more advertising packets from the second device and connecting to the second device.

11. The analyte monitoring system of claim 1, wherein the two or more devices further include a third device, and the transceiver is further configured to establish a connection with the third device only while being connected with no other device of the two or more devices and convey or receive third information to or from the third device while connected with the third device.

12. The analyte monitoring system of claim 1, wherein the second device comprises an insulin pump, a blood glucose meter, or a wearable.

13. The analyte monitoring system of claim 1, wherein the transceiver is further configured to calculate an analyte level using at least the received measurement information, the first information includes the calculated analyte level, and the analyte level displayed by the display device is the calculated analyte level.

14. The analyte monitoring system of claim 1, wherein the first information includes the measurement information, and the display device is further configured to calculate the displayed analyte level using at least the measurement information.

15. A display device comprising:
a transceiver interface configured to receive first information from a transceiver;
a user interface; and
a computer including a non-transitory memory and a processor, wherein the computer is configured to (i) use the transceiver interface to establish a connection with the transceiver, (ii) use the transceiver interface to receive an analyte level from the transceiver while connected with the transceiver, (iii) cause the user interface to display an analyte level based on at least the first information, and (iv) use the transceiver interface to terminate the connection with the transceiver if any of one or more disconnection events occur, wherein the one or more disconnection events include detecting an available connection with a second device.

16. The display device of claim 15, wherein the computer is further configured to execute a mobile medical application (MMA), and the one or more disconnection events include the MMA transitioning from being run in the foreground to running in the background.

17. The display device of claim 15, wherein the computer is further configured to use the transceiver interface to establish the connection with the transceiver by receiving one or more advertising packets from the transceiver and connecting to the transceiver.

18. The display device of claim 15, wherein the displayed analyte level is included in the first information.

19. The display device of claim 15, wherein the first information includes measurement information, and the computer is further configured to calculate the displayed analyte level using at least the measurement information.

20. A method of using an analyte system including an analyte sensor, a transceiver, and two or more devices including a display device and a second device, the method comprising:
using the transceiver to receive measurement information from the analyte sensor;
using the transceiver to establish a connection with the display device while being connected with no other device of the two or more devices;

using the transceiver to convey first information to the display device while connected with the display device;
using the display device to receive the first information from the transceiver and display an analyte level based on at least the first information;
using the transceiver to establish a connection with the second device while being connected with no other device of the two or more devices;
using the transceiver to convey or receive second information to or from the second device while connected with the second device;
using the second device to receive or convey the second information from or to the transceiver; and
using the display device to terminate the connection with the transceiver if any of one or more disconnection events occur, wherein the one or more disconnection events include the display device detecting an available connection with the second device.

21. The method of claim 20, further comprising using the display device to execute a mobile medical application (MMA), and the one or more disconnection events include the MMA transitioning from being run in the foreground to running in the background.

22. The method of claim 20, further comprising
using the transceiver to establish the connection with the second device in response to the display device terminating the connection with the transceiver.

23. The method of claim 20, further comprising:
using the transceiver to store an identification of each of the two or more devices in a memory of the transceiver; and
using the transceiver to transition between connections with the identified two or more devices at scheduled intervals.

24. The method of claim 20, further comprising using the transceiver to transition from being connected to the display device to being connected to the second device and from being connected to the second device to being connected to the display device at scheduled intervals.

25. The method of claim 24, further comprising using the transceiver to transition from being connected to the second device to being connected to the display device by terminating the connection with the second device and establishing the connection with the display device.

26. The method of claim 24, further comprising using the transceiver to transition from being connected to the display device to being connected to the second device by terminating the connection with the display device and establishing the connection with the second device.

27. The method of claim 20, further comprising using the transceiver to establish the connection with the display device by conveying one or more advertising packets and waiting for the display device to connect to the transceiver.

28. The method of claim 20, further comprising using the transceiver to establish the connection with the second device by conveying one or more advertising packets and waiting for the second device to connect to the transceiver.

29. The method of claim 20, further comprising using the transceiver to establish the connection with the second device by receiving one or more advertising packets from the second device and connecting to the second device.

30. The method of claim 20, wherein the two or more devices further include a third device, and the method further comprises using the transceiver to establish a connection with the third device while being connected with no other device of the two or more devices and convey or receive third information to or from the third device while connected with the third device.

31. The method of claim 20, further comprising using the transceiver to calculate an analyte level using at least the measurement information, wherein the first information includes the calculated analyte level, and the analyte level displayed by the display device is the calculated analyte level.

32. The method of claim 20, wherein the first information includes the measurement information, and the display device is further configured to calculate the displayed analyte level using at least the measurement information.

33. The analyte monitoring system of claim 1, wherein none of the two or more devices is the analyte sensor.

34. The method of claim 20, wherein none of the two or more devices is the analyte sensor.

* * * * *